United States Patent [19]

Kato et al.

[11] 4,258,219

[45] Mar. 24, 1981

[54] PROCESS FOR PRODUCING HYDROQUINONE

[75] Inventors: Nobukatsu Kato, Tokai; Tsutomu Takase, Nagoya; Yoshio Morimoto, Tokai, all of Japan

[73] Assignee: Mitsui Toatsu Chemicals, Inc., Tokyo, Japan

[21] Appl. No.: 86,666

[22] Filed: Oct. 19, 1979

[30] Foreign Application Priority Data

| Oct. 27, 1978 | [JP] | Japan | 53-131710 |
| Oct. 27, 1978 | [JP] | Japan | 53-131711 |
| Oct. 27, 1978 | [JP] | Japan | 53-131712 |
| Oct. 31, 1978 | [JP] | Japan | 53-133166 |
| Nov. 15, 1978 | [JP] | Japan | 53-139808 |

[51] Int. Cl.$^3$ .............................................. C07C 37/01
[52] U.S. Cl. .................................................... 568/771
[58] Field of Search .................. 568/771; 260/586 P, 260/593 R, 593 N

[56] References Cited

U.S. PATENT DOCUMENTS

| 3,849,502 | 11/1974 | Bourdin et al. | 568/771 |
| 4,045,496 | 8/1977 | Seifert | 568/771 |
| 4,078,006 | 3/1978 | Umemeura et al. | 568/771 |

FOREIGN PATENT DOCUMENTS 1344602  1/1974  United Kingdom ................... 568/771

*Primary Examiner*—Werren B. Lone
*Attorney, Agent, or Firm*—Cushman, Darby & Cushman

[57] ABSTRACT

An improved process for producing hydroquinone from p-isopropenyl phenol is disclosed. Hydroquinone is obtained by oxidizing p-isopropenyl phenol with hydrogen peroxide or an organic peroxide as an oxidizing agent at a temperature of 28° to 50° C. in the presence of a strong acid catalyst using a slightly or hardly water-soluble high-boiling polar solvent. In the oxidation reaction, the mole ratio of the oxidizing agent to p-isopropenyl phenol is kept at less than 1. After the reaction, in order to effectively decompose or consume the undecomposed p-isopropenyl phenol hydroperoxide and the unreacted oxidizing agent remaining in the reaction mixture, the reaction mixture is aged. Alternatively, or subsequently to the aging reaction, $SO_2$ is added to the reaction mixture to completely decompose the undecomposed or unreacted peroxide. Thus, hydroquinone of high purity is obtained.

20 Claims, No Drawings

PROCESS FOR PRODUCING HYDROQUINONE

BACKGROUND OF THE INVENTION

Oxidation of para-substituted phenols was suggested as a method for commercial production of hydroquinone (Japanese Patent Publication No. 36739/1976). The present inventors previously suggested an improved method in which p-isopropenyl phenol in a slightly or hardly water-soluble high-boiling polar solvent is used as a starting material in the above-mentioned method (Japanese Laid-Open Patent Publication No. 106929/1975). On further investigation, the present inventors found that in order to practice this method commercially, it is very important to control the oxidation reaction temperature properly. The specification of the above-cited Japanese Patent Publication No. 36739/1976 states that the starting p-isopropenyl phenol is mixed with a peroxide at about 20° C., a strong acid is added to this mixture, and the resulting mixture is maintained at a temperature in the range of about 10° C. to about 40° C. to perform the reaction. However, the present inventors energetically and detailedly studied the effect of the oxidation reaction temperature on the reaction, and found that according to such a temperature control, the peroxide of the starting p-isopropenyl phenol sometimes builds up in the reaction system, and abruptly decomposes to induce a vigorous exothermic reaction, thus causing troubles to the commercial practice of the reaction. It was also found that when as shown in specification of the above-cited Japanese Patent Publication No. 36739/1976, the mole ratio of the peroxide to the starting p-isopropenyl phenol is 1 to 1.5, adverse effects are exerted on the yield and purity of hydroquinone. The present inventors also discovered that as the catalyst for the oxidation reaction, a strong acid having a pKa value of not more than about 1.0 is used as disclosed in the above-cited Japanese Patent Publication, but depending upon its concentration, it may adversely affect the yield and purity of hydroquinone, and the formation of a hydroperoxide of p-isopropenyl phenol during the reaction. Furthermore, the reaction mixture left after substantial termination of the reaction still contains the unreacted oxidizing agent and the hydroperoxide of p-isopropenyl phenol, a reaction intermediate. If these compounds are left as they are, they will react with the resulting hydroquinone to form impurities such as benzoquinone, and cause a reduction in the yield of hydroquinone.

Extensive investigations of the present inventors in an attempt to solve these problems have now led to the accomplishment of the present invention.

SUMMARY OF THE INVENTION

This invention relates to an improved process for producing hydroquinone having a reduced content of impurities such as benzoquinone from p-isopropenyl phenol.

The present invention is directed to a process for producing hydroquinone by the oxidation of p-isopropenyl phenol, which is characterized by the following.

(1) p-isopropenyl phenol, a slightly or hardly water-soluble high-boiling polar solvent, a strong acid and hydrogen peroxide or an organic peroxide are fed at a temperature of at least 25° C. but below the reaction temperature, and the oxidation reaction of the p-isopropenyl phenol is carried out at a temperature in the range of 28° C. and 50° C.

(2) p-isopropenyl phenol is reacted with a smaller amount in moles of hydrogen peroxide or an organic peroxide in the presence of a slightly or hardly water-soluble high-boiling polar solvent and a strong acid.

(3) The concentration of the strong acid used as a catalyst for the oxidation reaction in (1) and (2) above is preferably at least 55%.

(4) The reaction mixture obtained by the oxidation reaction by the method (1) and/or (2) is then subjected to an aging reaction at a temperature of 30° C. to 50° C.

(5) The reaction mixture obtained by the oxidation reaction (1) and/or (2) is treated with sulfurous acid in an amount at least equimolar to the hydrogen peroxide or organic peroxide remaining in the reaction mixture.

DETAILED DESCRIPTION OF THE INVENTION

The oxidation reaction of p-isopropenyl phenol in the process for producing hydroquinone in accordance with this invention is carried out using hydrogen peroxide or an organic peroxide as an oxidizing agent in the presence of a strong acid in a slightly or hardly water-soluble high-boiling polar solvent; characterized in that a solution of p-isopropenyl phenol, the strong acid and the hydrogen peroxide or organic peroxide are fed into an oxidation reaction zone maintained at a temperature of at least 25° C., then oxidation reaction of the p-isopropenyl phenol with the oxidizing agent is carried out at a temperature in the range of 28° C. to 50° C., the mole ratio of the hydrogen peroxide or organic peroxide to p-isopropenyl phenol is maintained at less than 1, and that preferably, the concentration of the strong acid is at least 55%.

The p-isopropenyl phenol as a starting material can be produced, for example, by a method which comprises cleaving dihydroxydiphenylpropane by heating it to at least 180° C. in the presence of a basic catalyst such as an oxide, hydroxide, alcoholate, phenolate, alkylcarboxylate, carbonate or hydride of an alkali metal, an alkaline earth metal, aluminum, zinc, cadmium or lead to obtain a mixture of phenol, p-isopropenyl phenol and oligomers of p-isopropenyl phenol, removing the phenol from the mixture, and heating the residue at a high temperature of at least 150° C. preferably under reduced pressure in the absence or presence of a basic catalyst such as sodium hydroxide or potassium hydroxide to cleave the oligomers of p-isopropenyl phenol and to generate p-isopropenyl phenol; or a method which comprises heating a mixture containing p-isopropyl phenol, p-isopropenyl phenol, oligomers of p-isopropenyl phenol, α-hydroxyisopropylphenol in the absence or presence of a basic catalyst thereby to cleave the oligomers of p-isopropenyl phenol and generate p-isopropenyl phenol, the aforesaid starting mixture being obtained as a by-product in the production of hydroquinone by air oxidation of p-diisopropylbenzene to synthesize p-diisopropylbenzene dihydroperoxide followed by acid cleavage thereof.

The p-isopropenyl phenol generated by these methods is contacted with a slightly or hardly water-soluble high-boiling polar solvent either in the gaseous state or after condensation to form a solution of the p-isopropenyl phenol which is to be fed to the oxidation reaction zone. Suitable slightly or hardly water-soluble high-boiling solvents are alcohols, esters and ketones which have a boiling point of at least 100° C., preferably at least 150° C., at 760 mmHg, and a solubility in water at room temperature of not more than 10% by weight, preferably not more than 2% by weight. Specific examples include aliphatic alcohols such as heptyl alcohol, n-octyl alcohol, 2-ethylhexyl alcohol, isooctyl alcohol, n-nonyl alcohol, isodecanol and tridecanol, esters such as butyl acetate, amyl acetate, 2-ethylhexyl acetate, cyclohexyl acetate, and diethylene glycol monobutyl ether acetate, and ketones such as ethylbutyl ketone, valerone (diisobutyl ketone), cyclohexanone and acetophenone.

Contacting of p-isopropenyl phenol with the polar solvent can be effected by various methods such as a method which comprises introducing the generated p-isopropenyl phenol in the gaseous state into an absorption tower, contacting it with the solvent near the top of the tower to cause it to be absorbed and dissolved in the solvent, and withdrawing it as a solution; a method which comprises contacting a condensed liquid of the generated p-isopropenyl phenol with the solvent in its path to a receiver, and withdrawing it as a solution; or a method which comprises conducting a condensed liquid of the p-isopropenyl phenol into a receiver having the solvent therein, dissolving it in the solvent, and withdrawing it as a solution. To perform the contacting with a good efficiency, the contacting of the p-isopropenyl phenol with the solvent should preferably be carried out near the inlet opening of the condenser. In the method in which the condensed liquid is contacted with the solvent, the time which elapses until the p-isopropenyl phenol contacts the solvent should preferably be as short as possible. It is within several minutes, preferably within 1 minute, after the condensation. The preferred amount of the high-boiling polar solvent is 1 to 10 times, usually 1 to 3 times, the weight of p-isopropenyl phenol.

Hydrogen peroxide and organic peroxide are used as an oxidizing agent for converting the p-isopropenyl phenol in the solution to hydroquinone. The organic peroxides are compounds of the general formula:

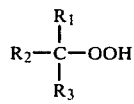

wherein $R_1$, $R_2$ and $R_3$ each represents an alkyl or aryl group. Examples of the organic peroxide are t-butyl hydroperoxide, cumene hydroperoxide and isopropylbenzene hydroperoxide.

A first important feature of the oxidation reaction in accordance with this invention is that in mixing the strong acid and the oxidizing agent with a solution of p-isopropenyl phenol, the reaction system is maintained at at least 25° C. but below the reaction temperature, and during the oxidation reaction, the reaction system is maintained at 28° to 50° C., preferably 30° to 45° C. The temperature of 28° C., the lower limit of the oxidation reaction temperature in the process of this invention, is a temperature at which the hydroperoxide of p-isopropenyl phenol formed by the oxidation of p-isopropenyl phenol abruptly decomposes into hydroquinone and acetone. At temperatures below this limit, the decomposition reaction is slow, and the buildup of the hydroperoxide of p-isopropenyl phenol in the reaction system increases. When the temperature of the reaction system rises to above 28° C. by the heat generated by the decomposition of the hydroperoxide, or when the temperature is raised to accelerate the decomposition, the decomposition reaction takes place abruptly, and the heat generated cannot be absorbed by usual methods. On the other hand, when the oxidation reaction temperature is above 50° C., the resulting hydroquinone undesirably changes to benzoquinone.

When the solution of p-isopropenyl phenol having the strong acid and the oxidizing agent mixed therewith is to be fed into the reaction system continuously, if the solution is pre-heated to a temperature near the reaction temperature which is set at 28° to 50° C., it can be fed while it is maintained at this temperature. However, when the reaction is to be performed batchwise, if the temperature of the solution to be fed is below 25° C., it should be fed after it is pre-heated to this temperature. Otherwise, the temperature control of the reaction system becomes difficult.

A second important feature of the oxidation reaction in accordance with the process of this invention is that the reaction is carried out while maintaining the mole ratio of the oxidizing agent to p-isopropenyl phenol at less than 1, preferably at 0.90 to 0.99, especially at 0.95 to 0.99. If the mole ratio is less than 0.90, p-isopropenyl phenol is oligomerized by the action of the strong acid catalyst to reduce the yield of hydroquinone. If it is 1 or more, the resulting hydroquinone is further oxidized to benzoquinone, etc. to reduce the purity of the resulting hydroquinone. This tendency is especially great when the reaction temperature is high.

The strong acid used as a catalyst for the oxidation reaction preferably has a pKa value of not more than about 1.0. Examples of the strong acid are sulfuric acid, hydrochloric acid, nitric acid and p-toluenesulfonic acid. The amount of the strong acid used is 1 to 100 mole%, especially 3 to 30 mole%, based on the p-isopropenyl phenol used. It is especially preferable in this case to use the strong acid in a concentration of at least 55%. The concentration of the strong acid greatly affects the formation of the hydroperoxide of p-isopropenyl phenol. When the concentration of the strong acid is less than 55%, the formation of p-isopropenyl phenol is undesirably accelerated.

The oxidation reaction step in the process of this invention is characterized by the prescribing of the reaction temperature as the first feature, and/or the limitation of the mole ratio of the oxidizing agent to p-isopropenyl phenol as the second feature.

By performing the process of this invention, the temperature control of the oxidation reaction system in the production of hydroquinone from p-isopropenyl phenol can be effected stably and safely by usual methods. In commercial operations, the starting material can be fed at an increased speed without the need for interrupting the feeding of the material for the control of the temperature of the reaction system. Thus, the process of this invention is especially suitable for a continuous operation. According to the process of this invention, the yield of the oxidation product is steadily more than 90%.

The reaction mixture obtained by performing the oxidation reaction for a predetermined period of time until it is substantially terminated contains small amounts of undecomposed p-isopropenyl phenol hydroperoxide and the unreacted oxidizing agent. Thus, a third feature of the process of this invention is that to completely decompose or effectively consume the undecomposed p-isopropenyl phenol hydroperoxide and the unreacted oxidizing agent in the reaction mixture, the reaction mixture after the reaction is subjected to an aging reaction at a temperature in the range of 30° to 50° C. A fourth feature of the process of this invention is that to remove the peroxide remaining in a trace amount, sulfurous acid is added to the reaction mixture after the reaction to treat it.

The reaction mixture obtained by the oxidation reaction in the process of this invention usually contains about 0.1 to 0.4% by weight of hydrogen peroxide and p-isopropenyl phenol hydroperoxide when hydrogen peroxide is used as the oxidizing agent.

According to the third feature of the present invention, the aging reaction is carried out by stirring the reaction mixture in an aging reaction zone at a temperature in the range of 30° to 50° C. to decompose or consume effectively the undecomposed material or the remaining peroxide. The aging time differs depending upon the treating temperature, but is usually 10 minutes to 1 hour. When the oxidation reaction temperature is relatively low, e.g. about 30° to 38° C., it is preferred to perform the aging treatment sufficiently. When the hydroquinone is to be produced batchwise, the aging can be effected in the same reaction subsequent to the oxidation reaction. When it is performed continuously, it is desirable to perform the aging treatment in a separately provided reaction vessel. The aging reaction serves to consume the remaining oxidizing agent (e.g., hydrogen peroxide) and to decompose the remaining hydroperoxide of isopropenyl phenol completely into hydroquinone and acetone, and thus contributes greatly to the increase of the yield of hydroquinone.

By the aging reaction, the content of the unreacted peroxide and the undecomposed p-isopropenyl phenol peroxide can be decreased to less than 0.1% by weight.

According to the fourth feature of the process of this invention, sulfurous acid is added to the reaction mixture after the oxidation reaction to remove the unreacted peroxide. Sulfur dioxide or its aqueous solution is added in an amount at least equimolar to the remaining oxidizing agent. This is because the sulfurous acid is consumed also for the reduction of the undecomposed hydroperoxide of p-isopropenyl phenol, and it also serves to prevent the oxidation of the hydroquinone in the reaction mixture by oxygen in the air. Use of a large excess of sulfur dioxide, however, is not desirable because it will cause corrosion of the reaction apparatus. Sulfur dioxide can also be used in the form of an aqueous solution. Preferably, however, it is directly blown into the reaction mixture.

When hydroquinone is to be produced continuously, it is desirable to combine the step of treating the reaction mixture after the reaction with the aging treatment, and perform the treatment in a sulfurous acid treating tank separately provided subsequent to the aging reaction tank. This combined process is advantageous because the amount of sulfurous acid can be reduced.

The process of this invention can afford hydroquinone with a reduced content of impurities in a high yield.

Examples are given below.

EXAMPLE 1

(1) Production of a solution of p-isopropenyl phenol

A distillation still was charged with 500 g of a phenol-free cleavage product of bisphenol A containing 8% of monomeric p-isopropenyl phenol, 85% of a linear dimer of p-isopropenyl phenol and 7% of trimers or higher oligomers of p-isopropenyl phenol.

The charge was heated under reduced pressure while raising the temperature of the inside of the still from 150° C. to 240° C. to distill p-isopropenyl phenol.

A short feeding section was provided at the inlet of a condenser tube, and 1000 g of n-octanol was continuously fed from the upper inlet opening of the feeding section. In view of the rate of distillation of p-isopropenyl phenol, the solvent was fed at a rate about twice as much as that of the distilled p-isopropenyl phenol. Within the packed tower, the distillate was absorbed and dissolved in the solvent, and withdrawn into a receiver as a solution in octanol. The composition of 1470 g (concentration 32%) of the withdrawn octanol solution was determined by gas chromatography and thin-layer chromatography. It was found that the solution did not contain dimer and oligomers of p-isopropenyl phenol.

The amount of monomeric p-isopropenyl phenol in the octanol solution was 470 g which corresponded to a cleavage yield of 94%.

(2) Production of hydroquinone 84 g (0.201 mole) of the resulting p-isopropenyl phenol solution, 21.46 g (0.188 mole) of 30% aqueous hydrogen peroxide, and 10.0 g of an octanol solution containing 2.00 g of 98% sulfuric acid were maintained respectively at about 35° C., and simultaneously and continuously added dropwise to a flask and mixed. The reaction was an exothermic reaction. By cooling, the temperature of the inside of the flask was maintained at 35° C.

After the addition, the mixture was stirred for 1 hour. Then, 25 g of sodium sulfite as a saturated aqueous solution was added to neutralize the sulfuric acid and decompose the unreacted peroxide. On standing, the reaction mixture separated into two layers. The aqueous layer was separated, and then, the organic layer was extracted four times with 150 ml of hot water each time. The water extracts containing acetone were combined, and concentrated, and cooled. The hydroquinone crystals obtained were collected by filtration, and dried to afford 19.3 g of hydroquinone having a purity of 99%. Hydroquinone and sodium sulfite in the filtrate were neutralized, and then hydroquinone in the separated aqueous layer was recovered. The total yield of hydroquinone, calculated as 100% hydroquinone, was 20.3 g (yield 97.2%).

COMPARATIVE EXAMPLE 1

In an attempt to charge 84 g of the p-isopropenyl phenol solution obtained in Example 1, 21.46 g of 30% aqueous hydrogen peroxide and 10.0 g of an octanol solution containing 2.00 g of 98% sulfuric acid, they were maintained at about 20° C., and mixed. When about 25% of the materials were charged, the temperature rose abruptly, and the mixture could no longer be properly cooled. Thus, the charging of these materials was stopped. The system was then cooled to 20° C., and when the remaining materials were charged, the temperature again rose abruptly. Thus, the charging of the materials was stopped again. Thus, it was necessary to give up the preparation of hydroquinone by the effective performance of the reaction.

EXAMPLE 2

111.4 g (0.266 mole) of the p-isopropenyl phenol solution obtained in Example 1, 29.7 g (0.262 mole) of 30% aqueous hydrogen peroxide and 4.87 g of 64.1% sulfuric acid were maintained respectively at about 35° C., and over the course of about 5 hours, simultaneously and continuously added dropwise to a flask and mixed. The reaction was an exothermic reaction. By cooling, the inside of the flask was maintained at 35° C.

After the addition, the mixture was stirred for 1 hour, and then, 4.0 g of sodium sulfite was added as a saturated aqueous solution to neutralize the sulfuric acid and decompose the unreacted peroxide.

The reaction mixture was separated into two layers by allowing it to stand. The aqueous layer was separated. The organic layer was extracted four times with 150 ml of hot water each time. The water extracts containing acetone were combined, concentrated, and cooled. The resulting hydroquinone crystals were separated by filtration, and dried to afford 26.8 g of hydroquinone having a purity of 99.9%. Hydroquinone and sodium sulfite in the filtrate were neutralized, and hydroquinone in the separated aqueous layer was recovered. The total amount of hydroquinone obtained, calculated as 100% hydroquinone, was 28.1 g (yield 97.5%).

COMPARATIVE EXAMPLE 2

111.4 g (0.266 mole) of the p-isopropenyl phenol solution obtained in Example 1, 39.1 g (0.345 mole) of 30% aqueous hydrogen peroxide and 4.87 g of 64.1% sulfuric acid were maintained at about 35° C., and over the course of about 5 hours, simultaneously and continuously added dropwise to a flask and mixed. The reaction was an exothermic reaction. By cooling, the temperature of the inside of the flask was maintained at 35° C.

After the addition, the mixture was stirred for 1 hour, and then, 17.1 g of sodium sulfite was added as a saturated aqueous solution to neutralize the sulfuric acid and decompose the unreacted peroxide.

The reaction mixture was allowed to stand to separate it into two layers. The aqueous layer was separated. The organic layer was extracted four times with 150 ml of hot water each time. The water extracts containing acetone were combined, concentrated, and cooled. The resulting hydroquinone crystals were separated by filtration, and dried to afford 24.0 g of hydroquinone having a purity of 70%. Hydroquinone and sodium sulfite in the filtrate were neutralized, and hydroquinone in the separated aqueous layer was recovered. The total amount of hydroquinone obtained, calculated as 100% hydroquinone, was 21.0 g (yield 71.7%).

EXAMPLE 3

300 g (0.716 mole) of the p-isopropenyl phenol solution obtained in Example 1, 78.7 g (0.694 mole) of 30% aqueous hydrogen peroxide and 17.5 g of 60% sulfuric acid were maintained at about 35° C., and over the course of about 5 hours, simultaneously and continuously added dropwise to a flask and mixed. The reaction was an exothermic reaction. By cooling, the temperature of the inside of the flask was maintained at 35° C.

After the reaction, the mixture was stirred for 1 hour, and then 13.5 g of sodium sulfite was added as a saturated aqueous solution to neutralize the sulfuric acid and decompose the unreacted peroxide.

The reaction mixture was allowed to stand to separate it into two layers. The aqueous layer was separated. The organic layer was extracted five times with 400 ml of hot water each time. The water extracts containing acetone were combined, concentrated, and cooled. The resulting hydroquinone crystals were separated by filtration, and dried to afford 73.3 g of hydroquinone having a purity of 99.5%. Hydroquinone and sodium sulfite in the filtrate were neutralized, and hydroquinone in the separated aqueous layer was recovered. The total amount of hydroquinone obtained, calculated as 100% hydroquinone, was 76.8 g (yield 98.5%).

COMPARATIVE EXAMPLE 3

300 g (0.716 mole) of the p-isopropenyl phenol solution obtained in Example 1, 97.2 g (0.858 mole) of 30% aqueous hydrogen peroxide and 49.1 g of 50% sulfuric acid were maintained at about 50° C., and over the course of about 5 hours, simultaneously and continuously added dropwise to a flask and mixed. The reaction temperature was maintained at 50° C.

After the addition, the mixture was stirred for 1 hour, and then 53.2 g of sodium sulfite was added as a saturated aqueous solution to neutralize the sulfuric acid and decompose the unreacted peroxide.

The reaction mixture was allowed to stand to separate it into two layers. The aqueous layer was separated. The organic layer was extracted five times with 400 ml of hot water each time. The water extracts containing acetone were combined, concentrated, and cooled. The resulting hydroquinone crystals were separated by filtration, and dried to afford 65.4 g of hydroquinone having a purity of 75%. Hydroquinone and sodium sulfite in the filtrate were neutralized, and hydroquinone in the separated aqueous layer was recovered. The total amount of hydroquinone obtained, calculated as 100% hydroquinone, was 51.6 g (yield 65.5%).

EXAMPLE 4

500 g (1.194 moles) of the p-isopropenyl phenol solution obtained in Example 1, 132.4 g (1.168 moles) of 30% aqueous hydrogen peroxide and 29.2 g of 60% sulfuric acid were maintained respectively at about 33° C., and over the course of about 5 hours, simultaneously and continuously added dropwise to a flask and mixed. The reaction was an exothermic reaction. By cooling, the temperature of the inside of the flask was maintained at 35° C.

After the addition, the mixture was stirred for 1 hour, and then 23.14 g of sodium sulfite was added as a saturated aqueous solution to neutralize the sulfuric acid and decompose the unreacted peroxide. The reaction mixture was allowed to stand to separate it into two layers. The aqueous layer was separated. The organic layer was extracted with 900 ml of hot water each time. The water extracts containing acetone were combined, concentrated, and cooled. The resulting hydroquinone crystals were separated by filtration, and dried to afford 124.0 g of hydroquinone having a purity of 99.0%. Hydroquinone and sodium sulfite in the filtrate were neutralized, and hydroquinone in the separated aqueous layer was recovered. The total amount of hydroquinone obtained, calculated as 100% hydroquinone, was 129.3 g (yield 98.5%).

EXAMPLE 5

500 g (1.194 moles) of the p-isopropenyl phenol solution obtained in Example 1, 134.0 g (1.182 moles) of 30% aqueous hydrogen peroxide, and 31.1 g of 60% sulfuric acid were maintained respectively at about 30° C., and over the course of about 5 hours, simultaneously and continuously added dropwise to a flask and mixed. The reaction was an exothermic reaction. By cooling, the temperature of the inside of the flask was maintained at 32° C.

After the addition, the mixture was stirred for 1 hour. The concentrations of the hydrogen peroxide and the hydro-peroxide of p-isopropenyl phenol in the reaction system were 0.03%, and 0.05%, respectively.

Then, 0.61 g (1.2 molar times the amount of the remaining peroxide) of sulfurous acid gas was added to decompose the remaining peroxide. The reaction mixture was allowed to stand to separate it into two layers. The aqueous layer was separated. The organic layer was extracted five times with 900 ml of hot water each time. The water extracts containing acetone were combined, concentrated, and cooled. The resulting hydroquinone crystals were separated by filtration, and dried to afford 125.0 g of hydroquinone having a purity of 99.1%. Hydroquinone in the separated aqueous layer was recovered. The total amount of hydroquinone obtained, calculated as 100% hydroquinone, was 128.6 g (yield 98.0%).

What is claimed is:

1. A process for producing hydroquinone, which comprises feeding p-isopropenyl phenol, a slightly or hardly water-soluble high-boiling polar solvent which is an alcohol selected from the group consisting of heptyl alcohol, n-octyl alcohol, 2-ethylhexanol, i-octyl alcohol, n-nonyl alcohol and decanol, a strong acid having a pKa value of not more than about 1.0, and hydrogen peroxide or an organic peroxide at a temperature of at least 25° C. but below the reaction temperature, and performing the oxidation reaction of the p-isopropenyl phenol at a temperature in the range of 28° C. to 50° C.

2. A process according to claim 1 wherein the strong acid is sulfuric acid, hydrochloric acid, nitric acid or p-toluenesulfonic acid.

3. A process according to claim 1 wherein the mole ratio of oxidizing agent to p-isopropenyl phenol is 0.90 to 0.99:1 and there is used 1 to 100 moles of oxidizing agent per mole of isopropenyl phenol.

4. A process for producing hydroquinone, which comprises reacting p-isopropenyl phenol with hydrogen peroxide or an organic peroxide in a smaller molar amount than the p-isopropenyl phenol in the presence of a slightly or hardly water-soluble high-boiling polar solvent which is an alcohol selected from the group consisting of heptyl alcohol, n-octyl alcohol, 2-ethylhexanol, i-octyl alcohol, n-nonyl alcohol and decanol, and a strong acid having a pKa value of not more than about 1.0 at a temperature in the range of 28° C. to 50° C.

5. A process according to claim 4 wherein the strong acid is sulfuric acid, hydrochloric acid, nitric acid or p-toluenesulfonic acid.

6. A process according to claim 4 wherein the mole ratio of oxidizing agent to p-isopropenyl phenol is 0.90 to 0.99:1 and there is used 1 to 100 moles of oxidizing agent per mole of isopropenyl phenol.

7. A process for producing hydroquinone, which comprises reacting p-isopropenyl phenol with hydrogen peroxide water-soluble high-boiling polar solvent which is an alcohol, selected from the group consisting of heptyl alcohol, n-octyl alcohol, 2-ethylhexanol, i-octyl alcohol, n-nonyl alcohol and decanol and a strong acid having a pKa value of not more than about 1.0, and hydrogen peroxide or an organic peroxide at a temperature of at least 25° C. but below the reaction temperature, the amount in moles of said hydrogen peroxide or the organic peroxide being smaller than that of p-isopropenyl phenol, and performing the oxidation reaction of the p-isopropenyl phenol at a temperature in the range of 28° C. to 50° C.

8. A process according to claim 7 wherein the strong acid is sulfuric acid, hydrochloric acid, nitric acid or p-toluenesulfonic acid.

9. A process according to claim 7 wherein the mole ratio of oxidizing agent to p-isopropenyl phenol is 0.90 to 0.99:1 and there is used 1 to 100 moles of oxidizing agent per mole of isopropenyl phenol.

10. The process of claim 7 wherein the concentration of said strong acid is at least 55%.

11. A process according to claim 10 comprising treating the reaction mixture from the oxidation reaction mixture with sulfur dioxide or its aqueous solution in a molar amount at least equal to that of the hydrogen peroxide or organic peroxide.

12. A process according to claim 11 wherein the organic peroxide has the formula

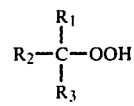

where $R_1$, $R_2$ and $R_3$ are alkyl or aryl.

13. A process according to claim 12 wherein there is employed hydrogen peroxide, t-butyl hydroperoxide, cumene hydroperoxide or isopropylbenzene hydroperoxide.

14. A process according to claim 12 wherein the mole ratio of oxidizing agent to p-isopropenyl phenol is 0.90 to 0.99:1.

15. A processing for producing hydroquinone, which comprises feeding p-isopropenyl phenol, a slightly or hardly water-soluble high-boiling polar solvent which is an alcohol selected from the group consisting of heptyl alcohol, n-octyl alcohol, 2-ethylhexanol, i-octyl alcohol n-nonyl alcohol and decanol, and a strong acid having a pKa value of not more than about 1.0 and hydrogen peroxide or an organic peroxide at a temperature of at least 25° C. but below the reaction temperature, performing the oxidation reaction of the p-isopropenyl phenol at a temperature in the range of 28° C. to 50° C., and then subjecting the resulting reaction mixture to an aging reaction at a temperature in the range of 30° C. to 50° C.

16. A process according to claim 15 wherein the strong acid is sulfuric acid, hydrochloric acid, nitric acid or p-toluenesulfonic acid.

17. A process according to claim 15 wherein the mole ratio of oxidizing agent to p-isopropenyl phenol is 0.90 to 0.99:1 and there is used 1 to 100 moles of oxidizing agent per mole of isopropenyl phenol.

18. A process for producing hydroquinone which comprises mixing p-isopropenyl phenol, a slightly or hardly water-soluble high-boiling polar solvent which is an alcohol selected from the group consisting of heptyl alcohol, n-octyl alcohol, 2-ethylhexanol, i-octyl alcohol, n-nonyl alcohol and decanol, a strong acid having a pKa value of not more than about 1.0 acid and hydrogen peroxide or an organic peroxide, performing the oxidation reaction of the p-isopropenyl phenol at a temperature in the range of 28° C. to 50° C. and then treating the reaction mixture with sulfur dioxide or its aqueous solution in an equimolar or larger amount to or than the hydrogen peroxide or the organic peroxide remaining in the reaction mixture.

19. A process according to claim 18 wherein the strong acid is sulfuric acid, hydrochloric acid, nitric acid or p-toluenesulfonic acid.

20. A process according to claim 18 wherein the mole ratio of oxidizing agent to p-isopropenyl phenol is 0.90 to 0.99:1 and there is used 1 to 100 moles of oxidizing agent per mole of isopropenyl phenol.

* * * * *